US00PP14401P39

(12) United States Plant Patent
Carruth

(10) Patent No.: US PP14,401 P3
(45) Date of Patent: Dec. 23, 2003

(54) HYBRID TEA ROSE PLANT NAMED 'WEKOSOMIT'

(50) Latin Name: *Hybrid Tea Rose*
Varietal Denomination: Wekosomit

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 62 days.

(21) Appl. No.: 10/055,742

(22) Filed: Oct. 25, 2001

(65) Prior Publication Data

US 2003/0084490 P1 May 1, 2003

(51) Int. Cl.[7] ..... A01H 5/00
(52) U.S. Cl. ..... Plt./134
(58) Field of Search ..... Plt./134

*Primary Examiner*—Howard J. Locker
(74) *Attorney, Agent, or Firm*—Christie, Parker & Hale, LLP

(57) ABSTRACT

A new variety of Hybrid Tea rose suitable for garden decoration, having flowers of clear pure Yellow coloration.

1 Drawing Sheet

BACKGROUND OF THE INVENTION

This invention relates to a new and distinct variety of Hybrid Tea Rose. The varietal denomination of the new variety is 'Wekosomit'. It has as its seed parent the variety known as 'DELosol' (not patented) and as its pollen parent the variety known as 'JACtou' (U.S. Plant Pat. No. 8,706).

SUMMARY OF THE INVENTION

Among the features which distinguish the new variety from other presently available and commercial rose cultivars known to the inventor are the following combination of characteristics: its green coloration of the large prickles on the branches and new shoots, its pure even yellow flower coloration, its filaments of varying color and its large fully double flowers. The new variety has a bushy to somewhat upright growing habit, suitable for outdoor garden decoration.

Asexual reproduction of the new variety by budding on the rootstock *Rosa hybrida* var. 'Dr. Huey' as performed in Kern County and Upland, Calif., shows that the foregoing and other distinguishing characteristics come true to form and are established and transmitted through succeeding propagation. 'Wekosomit' may be asexually propagated by cuttings, budding and grafting.

COMPARISON WITH PARENTS

The new variety may be distinguished from its seed parent, 'DELosol' by the following combination of characteristics: whereas 'DELosol' bears medium sized flowers on short to medium length stems, 'Wekosomit' bears significantly larger flowers on longer stems. The new variety has a bushy somewhat upright medium-tall mature growth habit, whereas the seed parent has a more spreading to rounded significantly shorter mature growth habit.

The new variety may be distinguished from its pollen parent, 'JACtou' by the following combination of characteristics: whereas 'Wekosomit' produces clear pure Yellow double flowers (about 39 to 44 petals) with large and nearly rounded petals, the pollen parent produces more Golden Yellow flowers with significantly less petalage (about 20 to 25) with significantly smaller and more obovate petals. 'JACtou' bears Dark Green foliage, whereas the new variety bears significantly Lighter Green foliage.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Royal Horticultural Society Colour Chart (1966) and terminology used in the color descriptions herein refers to plate numbers in this color chart except where common terms of color definition are employed.

DESCRIPTION OF THE NEW VARIETY

The following description is of 3 to 4 year-old plants of the new variety grown outdoors in Upland, Calif. in the month of August. Phenotypic expression may vary with environmental, cultural and climatic conditions, as well as differences in conditions of light and soil.

FLOWER

The new variety usually bears its flowers singly, sometimes in clusters of 2 to 3 per stem. Flowers may be borne in irregular flat to slightly rounded clusters on medium length stems (about 46 to 85 cm). Outdoors, the plant blooms abundantly and nearly continuously during the growing season. The flowers have a slight fruity fragrance.

BUD

The peduncle is about 3.9 to 5.9 cm in length, of somewhat slender to average in caliper (about 0.2 to 0.45 cm in diameter), and usually erect. It is moderately rough, with many stipitate glands, and very few hairs. Peduncle color is between 144A and 148C sometimes lightly suffused, especially on the side exposed to the sun, with between 187B and 183D.

Before the calyx breaks, the bud is about 1.6 to 2.2 cm in diameter at the widest point, about 1.8 to 2.5 cm in length, and very pointed to slightly ovoid in shape. The surface of the bud bears few foliaceous appendages and many stipitate glands, usually with slender somewhat cut foliaceous parts extending beyond the tip of the bud about ½ or more of its length. Bud color is between 144A and 138B sometimes lightly suffused, especially on the side exposed to the sun, with between 187B and 183D.

The sepals are about 3.2 to 4.2 cm in length and about 0.7 to 1.2 cm in width at the widest point. The outer surface of the sepal is between 144A and 138B sometimes lightly suffused, especially on the side exposed to the sun, with between 187B and 183D. The inner surface of the sepal is between 148C and 139D and covered with fine wooly tomentum; sepal margins are lined with many stipitate glands and numerous hairs.

As the petals open (after the calyx breaks), the bud is about 2.1 to 2.7 cm in diameter at the widest point, about 2.7 to 3.8 cm in length, and more broadly ovoid to somewhat pointed in form.

The color of the under surfaces of the newly opened petals is between 8B and 14D. The color of the upper surfaces of the newly opened petals is between 9B and 14C. There is no visible change in coloration at the point where the petal attaches.

BLOOM

When fully open, the bloom ranges from about 9.7 to 13.6 cm in diameter. Petalage is double with about 39 to 44 petals and about 5 to 7 petaloids arranged irregularly.

When partially open, the bloom form is moderately cupped to somewhat high centered, and the petals are moderately spiraled to somewhat cupped with petal edges moderately reflexed outward.

When fully open, the bloom form is more flat to somewhat cupped, and the petals are more loosely cupped with petal edges moderately reflexed outward.

PETALS

The substance of the petals is slightly leathery and moderately thin, with upper surfaces moderately satiny and under surfaces slightly shiny to matte.

The outer petals are broadly obovate to nearly round in shape, mostly with rounded apices.

The inner petals are more obovate to somewhat rounded in shape, mostly with rounded apices. Sometimes the petal apices are notched with 2 or more notches. The petals are about 4.0 to 4.8 cm in length and about 3.3 to 5.0 cm in width at the widest point.

Petal margins are mostly entire to sometimes slightly crenate.

NEWLY OPENED FLOWER

The under surface of the outer petals is between 8C and 14D. The upper surface of the outer petals is between 6C and 14C. There is no visible change in coloration at the point where the petal attaches.

The under surface of the intermediate and inner petals is between 12C and 14D. The upper surface of the intermediate and inner petals is between 7B and 14C. There is no visible change in coloration at the point where the petal attaches.

The general tonality of the newly opened flower is between 6C and 14C.

THREE-DAY-OLD FLOWER

The under surface of the outer and inner petals is between 10D and 11C.

The upper surface of the outer and inner petals is between 6D and 11C.

There is no visible change in coloration at the point where the petal attaches.

The general tonality of the three-day-old flower is between 6D and 11C.

On the spent bloom, the petals usually drop off cleanly.

In August in Upland, Calif., blooms on the bush growing outdoors generally last about 4 to 5 or more days. Cut roses from plants grown outdoors and kept at normal indoor living temperatures generally last about 4 to 5 or more days.

MALE REPRODUCTIVE ORGANS

Stamens are average in number (average about 100) and are arranged regularly about the pistils; a few are mixed with petaloids.

The filaments are of medium length (about 0.5 to 0.8 cm), most with anthers. Filaments vary in color. The outermost are between 12B and 13B in color and the innermost are between 44B and 45B in color.

The anthers are of medium size for the class and all open approximately at the same time. Anther color is between 21B and 17B when immature and between 165B and 200B at maturity.

Pollen is abundant.

FEMALE REPRODUCTIVE ORGANS

Pistils vary in number (average about 140).

The styles are moderately uneven, somewhat long in length (about 0.6 to 0.9 cm), moderately thin in caliper, and bunched at the base. Stigma color is near 12C. Style color is near 2D at the base suffusing to near 47B near the top.

Ovaries are all enclosed in the calyx.

Hips have not been observed on this variety when grown in Upland, Calif.

FOLIAGE

The compound leaves are usually comprised of 3 to 5 or more leaflets and are borne abundantly. The 5-leaflet leaves are about 10.6 to 11.9 cm in length and about 8.7 to 9.8 cm in width at the widest point, moderately leathery in texture, and semi-glossy to slightly matte in finish. The terminal leaflets are about 5.1 to 6.3 cm in length and about 3.4 to 4.0 cm in width at the widest point, shaped moderately ovate to somewhat oval with acute to slightly acuminate apices and rounded bases.

The margins of the leaves are simply serrate.

The upper surface of the mature leaf is between 137A and 138A. The under surface of the mature leaf is between 146B and 138B.

The upper surface of the young leaf is between 144A and 138B, sometimes lightly suffused with between 187B and 183C. The under surface of the young leaf is between 138B and 138C, sometimes heavily suffused with between 187B and 183C.

The rachis is moderately light in caliper and moderately rough. The upper side is moderately grooved with few hairs and some stipitate glands on the edges of the grooves. The under side of the rachis is moderately rough with few stipitate glands and some small prickles. The rachis color is between 144B and 138C.

The stipules are about 1.6 to 2.0 cm in length and medium to somewhat wide (about 0.4 to 0.6 cm) with medium length straight points that usually turn out at an angle of less than 90 degrees and sometimes slightly recurve toward the stem. The stipule color is between 144B and 138C.

The petiole is about 0.9 to 1.5 cm in length and about 0.1 to 0.2 cm in diameter at the widest point. The petiole color is between 144B and 138C.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a bushy somewhat upright medium height growing habit (about 160 to 210 cm in height and about 135 to 160 cm spread at the widest point), with very full branching. It displays moderately vigorous growth and the canes are of medium caliper for the class.

The color of the major stems is between 144B and 146C. They bear many large prickles that are about 0.9 to 1.3 cm in length.

The large prickles are almost straight and angled slightly downward with a medium length oval base; prickle color is between 166B and 175C. The major stem bears very few small prickles of similar shape and coloration.

The color of the branches is between 146A and 138B. They bear many large prickles which are of similar size and shape to the large prickles on the major stems; prickle color is between 144B and 145A. The branches bear few small prickles of similar shape and coloration.

The color of the new shoots is between 144A and 138B sometimes lightly suffused with between 187B and 183C. They bear many large prickles which are of similar size and shape to the large prickles on the major stems; prickle color is between 144B and 145A, often moderately suffused at the base with between 187B and 183C. The shoots bear some small prickles of similar shape and coloration.

I claim:

1. A new and distinct hybrid tea rose plant of the variety substantially as described and illustrated herein.

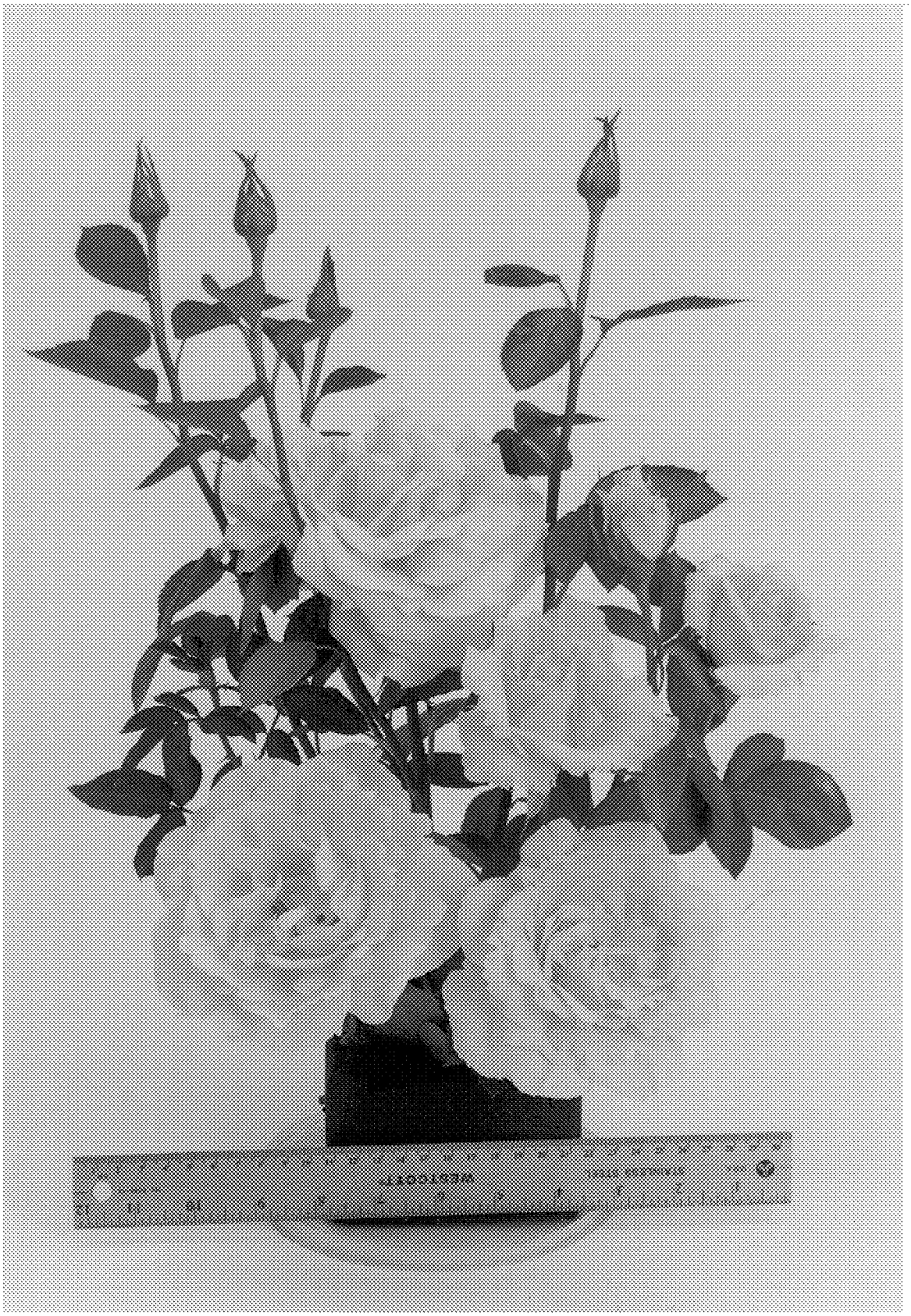

* * * * *